United States Patent

Mashak

[11] Patent Number: 5,509,405
[45] Date of Patent: Apr. 23, 1996

[54] PUMP FLOW VAPORIZER

[75] Inventor: James N. Mashak, Sun Prairie, Wis.

[73] Assignee: Ohmeda Inc., Liberty Corner, N.J.

[21] Appl. No.: 342,549

[22] Filed: Nov. 21, 1994

[51] Int. Cl.⁶ .................................................. A61M 15/00
[52] U.S. Cl. ................................ 128/203.12; 128/200.14; 261/76
[58] Field of Search .......................... 128/200.14, 200.21, 128/200.23, 203.12, 204.13, 204.14, 202.22; 261/76, 112.1, 118

[56] References Cited

U.S. PATENT DOCUMENTS

| | | | |
|---|---|---|---|
| 2,116,999 | 5/1938 | Ashby | 261/112.1 |
| 2,562,096 | 7/1951 | Herrman | 261/76 |
| 3,689,237 | 9/1972 | Stark et al. | 261/118 X |
| 3,841,560 | 10/1974 | Sielaff | 239/136 |
| 4,010,748 | 3/1977 | Dobritz | 128/203.27 |
| 4,026,285 | 5/1977 | Jackson | 128/200.17 |
| 4,430,994 | 2/1984 | Clawson et al. | 128/203.27 |
| 4,541,966 | 9/1985 | Smith | 261/27 |
| 4,587,966 | 5/1986 | Albarda | 128/202.22 |
| 5,092,326 | 3/1992 | Winn et al. | 128/205.13 |

Primary Examiner—Christopher A. Bennett
Assistant Examiner—Eric P. Raciti
Attorney, Agent, or Firm—Roger M. Rathbun; R. Hain Swope; Larry R. Cassett

[57] ABSTRACT

A vaporizer for introducing a vapor of an anesthetic liquid into t carrier gas for introduction into a patient is disclosed. The vaporizer directly vaporizes the liquid by introducing the liquid into a vaporizing chamber having an extremely large width to height ratio, i.e. in excess of 600:1. The carrier gas flows in laminar flow through the vaporizing chamber and the liquid anesthetic is introduced at a controlled flow such that it immediately vaporizes upon introduction to the entrance of the vaporizing chamber. A control scheme utilizing a CPU controls the percentage of anesthetic vapor in the outlet gas by sensing certain parameters and then controlling the flow of liquid anesthetic by controlling the speed of a controllable speed pump.

11 Claims, 1 Drawing Sheet

PUMP FLOW VAPORIZER

BACKGROUND OF THE INVENTION.

The present invention relates to an apparatus for vaporizing a liquid and, more particularly, to a vaporizer that receives carrier gas and vaporizes a liquid anesthetic agent with that carrier gas to produce a stream of carrier gas containing a known concentration of anesthetic agent for introduction into a patient.

There are, of course, various methods and means of vaporizing anesthetic agents to provide an anesthetizing gas to a patient. Typical of one of the types, include that described in U.S. Pat. No. 4,059,657 of Hay. More recently, with the introduction of an anesthetic agent having a relatively low boiling point, newer methods of vaporizing anesthetic agents have been devised and one such method and apparatus is described in U.S. Pat. No. 5,146,915 of Montgomery.

In the typical current anesthetic vaporizers, the unit contains a sump where liquid anesthetic is maintained and which also includes various wicks that provide a surface for enhancing the vaporization of that anesthetic. An inlet receives the carrier gas from a pressurized source, and generally, the stream of carrier gas is divided in the vaporizer such that a main stream of carrier gas continues toward the outlet while a bypass stream is diverted from the main stream and which enters the vaporizing chamber and picks up anesthetic vapor from the sump and wick arrangement. That bypass stream, now saturated with anesthetic later recombines with the main stream of carrier gas to pass through the outlet to be administered to a patient.

Control of the amount of anesthetic vapor in such vaporizers is accomplished by changing the amount of flow in the bypass flow path as a proportion of the carrier gas that passes through the vaporizer. As can be seen with reference to the cited prior art patents, the vaporizers, therefore, required a sump and which had to be at least of sufficient volume to contain enough liquid anesthetic to be used in the operating room during an operation. In addition, the mass of the vaporizers was also somewhat large to maintain, to the extent possible, a constant temperature throughout the operation of the vaporizer.

Such vaporizers are limited to relatively low flows due to the need to saturate the by pass stream with liquid agent before recombining with the main stream of carrier gas and, as noted, the vaporization occurred in a by pass stream, generally of a small proportion as opposed to the main stream. Thus the overall flow is limited and the vaporizing chamber itself must be separate from the main path of the carrier gas passing through the vaporizer.

Accordingly, such present vaporizers are generally large, heavy in mass and are somewhat limited in their ability to provide high flows of an anesthetic laden gas to a desired use.

SUMMARY OF THE INVENTION

In accordance with the present invention, an anesthetic vaporizer is provided and which overcomes the difficulties and problems heretofore associated with anesthetic vaporizers. In particular, the present vaporizer provides direct vaporization of the anesthetic into the main flow of carrier gas and does not, therefore, include a bypass stream in order to create and deliver a suitable anesthetizing mixture to the patient. In the present invention, a vaporizing chamber is of a specific shape, that is, having an extremely large width to height ratio and the carrier gas is introduced into that special vaporizing chamber. The flow of carrier gas through the vaporizing chamber is basically a laminar flow.

The liquid anesthetic is introduced directly into that main laminar flow of carrier gas through one or more specially constructed openings and at those openings, vaporization occurs immediately as the liquid reaches the vaporizing chamber. Due to the particular configuration of the opening or openings for the liquid anesthetic agent, a large gas/liquid interface area is formed inside the vaporizing chamber at the entrance of the opening(s). It is important to note that the liquid anesthetic does not enter the vaporizing chamber to any real extent as the flow is controlled such that the liquid is vaporized immediately as it enters the vaporizing chamber and only a meniscus is formed at the entrance to the vaporizing chamber. Thus, the gas/liquid interface provides immediate vaporization at the entrance to the vaporizing chamber.

Again, due to the extremely small height of the vaporizing chamber, the volume of carrier gas passing through the vaporizing chamber instantly vaporizes the liquid anesthetic agent immediately upon entrance into the vaporizing chamber. The liquid anesthetic is therefore delivered directly to the vaporizing chamber under a positive pressure, such as by a pump, and the supply of liquid anesthetic may, therefore, be at some more remote location. Accordingly, the anesthetic vaporizer itself does not contain, nor need, a sump for containing the liquid anesthetic.

Control of the concentration of anesthetic vapor in the outlet gas is easily achieved by controlling the main flow of the carrier gas and the flow of the liquid anesthetic. That control may be carried out by the design of the number and size of openings through which the liquid anesthetic passes to reach the vaporizing chamber as well as by controlling the pressure of the liquid anesthetic that is so introduced.

By means of the present vaporizer, therefore, high flows are attainable and the liquid is directly vaporized in a vaporizing chamber, thereby eliminating the need for bypass streams, proportioning valves and the like within the vaporizer. Additionally, the supply of liquid need not be provided by a large sump as part of the vaporizer.

DETAILED DESCRIPTION OF THE INVENTION

Figure 1:
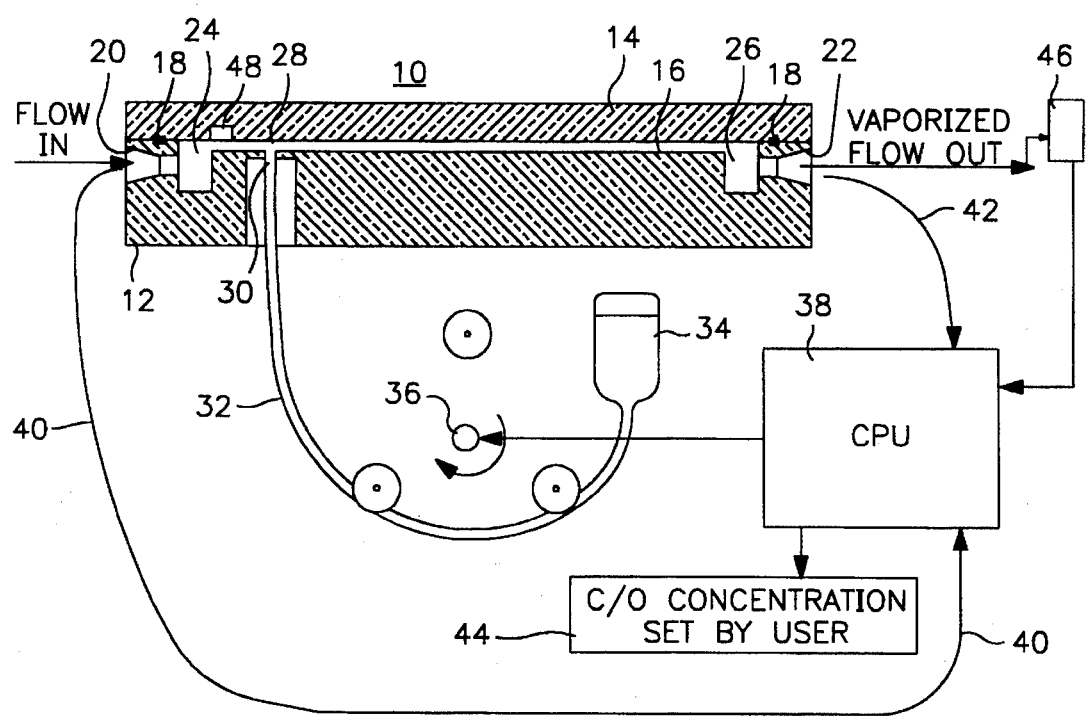
FIG. 1 is a cross-sectional schematic view of an anesthetic vaporizer constructed in accordance with the present invention.
Figure 2:
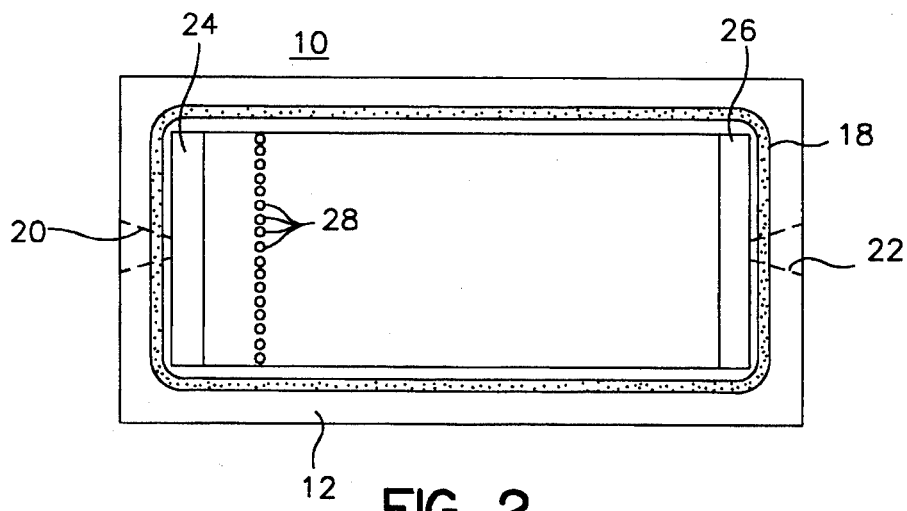
FIG. 2 is a top schematic view of the vaporizer of FIG. 1

Referring now to FIGS. 1 and 2, there is shown schematic views of a side cross-section and a top view of the anesthetic vaporizer constructed in accordance with the present invention and which shows the anesthetic vaporizer assembly 10 comprising a base 12 and a cover 14, the latter of which may be of a transparent material such as a high strength polycarbonate to enable the user to view the interior of the anesthetic vaporizer assembly 10 to monitor any build-up of material that could impede the performance of the anesthetic vaporizer assembly 10.

Intermediate the cover 14 and the base 12, there is formed a vaporizing chamber 16 and which, in the preferred embodiment, is an elongated chamber, rectangularly shaped.

As noted, the vaporizing chamber 16 is encircled by a gasket 18 to seal its periphery between cover 14 and base 12. As an important feature of the present invention, the ratio between the length of the vaporizing chamber 16 to its height is at least a predetermined value such that the vaporizing chamber 16 is extremely narrow so as to promote laminar flow of the gas passing therethrough and to increase the boundary layer, that is, the contact with the walls of the vaporizing chamber 16.

In the preferred embodiment, the vaporizing chamber 16 is rectangular shaped, however, it may also be a circular or annular shape providing the width to height ratio is maintained at least at the predetermined value.

An inlet 20 is formed in the anesthetic vaporizer assembly 10 and which receives a carrier gas, such as oxygen and which carrier gas picks up anesthetic vapor to produce a mixture of carrier gas/anesthetic vapor for administration to a patient. Likewise, an outlet 22 is formed at the opposite end of the vaporizing chamber 16 from the inlet 20 and which channels the flow of anesthetic laden carrier gas from the vaporizer assembly 10.

As can be seen, therefore, the vaporizing chamber 16 is a passage that communicates between the inlet 20 and the outlet 22 and therefore receives carrier gas from the inlet 20 and delivers that gas to the outlet 22. To stabilize the flow of gas through the vaporizer assembly, there may also be an inlet plenum 24 and an outlet plenum 26.

Again, in the preferred embodiment, the width of the vaporizing chamber 16 is about 3.0 inches and the height thereof is about 0.003 inches, therefore the overall width to height ratio is about 1000:1. It is preferred that the width to height ratio be at least 600:1 to achieve the desirable flow of gas through the vaporizing chamber 16 and to enhance the vaporization of liquid anesthetic therein.

The liquid anesthetic is preferably supplied to the vaporizing chamber 16 by means of a plurality of holes 28 formed in the base 12 and which communicate between a manifold 30 to the interior of the vaporizing chamber 16. As may be seen in FIG. 2, in particular, in the preferred embodiment, the plurality of holes 28 are formed aligned in a row and which row is generally perpendicular to the flow of gas passing through the vaporizing chamber 16. The uniform distribution of the holes 28 is important to insure that a uniform mixture of the vaporized liquid anesthetic enters the stream of carrier gas. As such, extremely minute holes are preferred, typical being about 0.005 inches in diameter and spaced about 0.020 inches apart centerline to centerline along the row. As a alternative, an extremely narrow slit may be employed to introduce the liquid and may be in the order of 0.002 inches wide.

The size of the opening that introduces the liquid anesthetic needs to be minute to obtain the desired distribution of liquid anesthetic and to insure that the liquid is vaporized immediately upon introduction into the vaporizing chamber 16.

A suitable conduit 32 delivers the liquid anesthetic agent to the manifold 30 from a reservoir 34 that contains the supply of liquid anesthetic agent. As may be seen, therefore, the reservoir 34 can readily be remote from the vaporizing chamber 16 and thus easy to fill, clean etc without disassembly of a vaporizer as is currently necessary in many vaporizers.

A pump 36 is located intermediate the reservoir 34 and the manifold 30 and which is precisely controllable in speed so as to afford control of the flow of liquid anesthetic agent being supplied to the manifold 30 and thus, obviously, to the holes 28 for introduction into the vaporizing chamber 16. A typical pump 36 suitable for the purpose is a peristaltic pump and which is readily controllable in speed to be sufficiently accurate for the use herein.

In general, therefore, the overall operation of the vaporizer of the present invention may be explained. The flow of carrier gas enters the inlet 20, and passes through the inlet plenum 24 where the flow is stabilized and distributed across the entrance to the vaporizing chamber 16. The vaporizing chamber 16 itself is generally rectangular in cross section and is extremely wide and thin, that is the width may be in the order of about 3.0 inches with its height being about 0.003 inches. Accordingly the overall width to height ratio is about 1000:1. It is important that such ratio be extremely high as will become apparent, typically a ratio in excess of 600 to 1. As such, the carrier gas entering into the vaporizing chamber 16 is rapidly converted to a laminar flow that is generally uniformly spread across the width of the opening to the vaporizing chamber 16.

The flow of carrier gas is therefore essentially laminar as it passes by the holes 28 through which the liquid anesthetic is introduced into the vaporizing chamber 16. The liquid anesthetic, pressurized by the pump 36 enters the vaporizing chamber 16 and is vaporized immediately. As indicated, at most, a meniscus of liquid is formed at the inlet to the vaporizing chamber 16 since vaporization is immediate as the liquid reaches vaporizing chamber 16. The flow of carrier gas is maintained at a predetermined flow passing through the vaporizing chamber 16 and the production of vapor is controlled by the flow of liquid anesthetic agent by the pump 36.

The anesthetic vapor is picked up by the carrier gas and is carried along the vaporizing chamber 16 to emerge from the outlet 22 as a carrier gas containing a desired amount of anesthetic vapor for introduction into a patient. The amount of vapor produced, and thus the concentration of vapor in the stream of gas delivered to the patient is readily controlled by controlling the pump 36, as will be explained.

As a typical control scheme for the vaporizer, a CPU 38 may be used and which gathers various data to control the pump 36. The CPU 38 gathers information via data line 40 indicating the pressure of carrier gas at the inlet 20 of the vaporizing chamber 16 as well as via data line 42 indicating the pressure of carrier gas/vapor exiting the vaporizing chamber 16 through the outlet 22. The measurement of pressures at data lines 40 and 42 represent the differential pressure across the vaporizing chamber 16 and both may be conventional pressure sensors. Since the flow is laminar, that differential pressure provides an accurate determination of the flow through the vaporizing chamber and which value can be used by the CPU 38 to determine the speed of the pump 36. CPU 38 also includes an input device, such as a keyboard 44 so that the user can set the desired concentration of anesthetic laden gas to be delivered to the patient. That set concentration thus determines the speed of the pump 36 and can be empirically determined, knowing the flow of the carrier gas through the vaporizing chamber 16, to set the proper speed of pump 36 to deliver the desired anesthetic concentration. As a further feature, a heater 48 may be placed at the entrance to the vaporizing chamber 16 to stabilize the temperature of the gas entering the vaporizing chamber 16.

To supplement the control, an agent sensor 46 of a standard commercial type may be located to determine the actual concentration of anesthetic in the gas to the patient and that value fed into the CPU 38. By a conventional feedback system, therefore, the agent sensor 46 may establish and control the desired concentration of anesthetic in the gas delivered to the patient.

While the present invention has been set forth in terms of a specific embodiment, it will be understood that the vaporizer herein disclosed may be modified or altered by those skilled in the art to other configurations. Accordingly, the invention is to be broadly construed and limited only by the scope and spirit of the claims appended hereto.

I claim:

1. An anesthetic vaporizer comprising an inlet for receiving carrier gas and an outlet for carrier gas and vaporized anesthetic agent for delivery to a patient, a vaporizing chamber forming a flow path between said inlet and said outlet, said vaporizing chamber comprising an elongated chamber having a large width to height ratio and forming a flow field for the flow of carrier gas therethrough, a liquid anesthetic agent inlet in said vaporizing chamber for admitting liquid anesthetic agent at a predetermined location into the flow of carrier gas through said vaporizing chamber, means for supplying liquid anesthetic agent to said liquid anesthetic agent inlet, and means for controlling the flow of the anesthetic agent supplied to said liquid anesthetic agent inlet to effect an immediate vaporization of the liquid anesthetic agent in said vaporizing chamber to control the concentration of vaporized anesthetic agent in the carrier gas delivered through said outlet to the patient.

2. An anesthetic vaporizer as defined in claim 1 wherein the width to height ratio is at least about 600:1.

3. An anesthetic vaporizer as defined in claim 1 wherein said width to height ratio is about 1000:1.

4. An anesthetic vaporizer as defined in claim 1 wherein said means for supplying liquid anesthetic agent comprises a controllable speed pump.

5. An anaesthetic vaporizer as defined in claim 4 wherein said controllable speed pump comprises a peristaltic pump.

6. An anesthetic vaporizer as defined in claim 4 wherein said means for controlling the flow of anesthetic agent comprises means to control the speed of said pump and which further includes a CPU and an input device to said CPU wherein said pump speed is determined by a signal from said input device to said CPU.

7. An anesthetic vaporizer as defined in claim 6 wherein said means to control the speed of said pump further includes an agent sensor adapted to sense the amount of anesthetic vapor in the stream of carrier gas from said outlet and provide a signal to said CPU indicative of such concentration and wherein said CPU uses such signal in determining the speed of said pump.

8. An anaesthetic vaporizer as defined in claim 1 wherein said liquid anesthetic agent inlet comprises a plurality of small openings entering into said vaporizing chamber.

9. An anesthetic vaporizer as defined in claim 8 wherein said small openings are aligned along a path generally perpendicular to the flow of carrier gas passing through said vaporizing chamber.

10. An anaesthetic vaporizer as defined in claim 9 wherein said openings are about 0.005 inches in diameter and the vaporizing chamber is rectangular in cross section.

11. An anesthetic vaporizer as defined in claim 8 wherein said vaporizing chamber is rectangular in cross-section having a width of about 3.0 inches and a height of about 0.003 inches.

* * * * *